United States Patent
Kawano et al.

(10) Patent No.: US 11,697,791 B2
(45) Date of Patent: Jul. 11, 2023

(54) CELL CULTURE SUBSTRATE, CULTURE VESSEL, METHOD FOR PRODUCING CELL CULTURE VESSEL, METHOD FOR ACQUIRING CELLS AND METHOD FOR CULTURING CELLS

(71) Applicants: Nikon Corporation, Tokyo (JP); UNIVERSITY PUBLIC CORPORATION OSAKA, Osaka (JP)

(72) Inventors: Takeshi Kawano, Hino (JP); Chie Kojima, Osaka (JP)

(73) Assignees: Nikon Corporation, Tokyo (JP); University Public Corporation Osaka, Osaka (JP)

(*) Notice: Subject to any disclaimer, the term of this patent is extended or adjusted under 35 U.S.C. 154(b) by 300 days.

(21) Appl. No.: 16/508,228

(22) Filed: Jul. 10, 2019

(65) Prior Publication Data

US 2020/0017815 A1  Jan. 16, 2020

Related U.S. Application Data (63) Continuation of application No. PCT/JP2018/000529, filed on Jan. 11, 2018.

(30) Foreign Application Priority Data

Jan. 12, 2017 (JP) ................. 2017-003427

(51) Int. Cl.
 C12M 1/12 (2006.01)
 C12M 1/00 (2006.01)
 C12N 5/00 (2006.01)

(52) U.S. Cl.
 CPC ............ *C12M 25/16* (2013.01); *C12M 23/20* (2013.01); *C12N 5/0068* (2013.01);
 (Continued)

(58) Field of Classification Search
 CPC .......... C12N 1/02; C12N 1/00; C12N 5/0068; C12N 2531/00; C12N 2529/10;
 (Continued)

(56) References Cited

U.S. PATENT DOCUMENTS

2015/0225686 A1  8/2015  Oshima et al.

FOREIGN PATENT DOCUMENTS

| JP | H11-349643 A | 12/1999 |
| JP | 2012-039947 A | 3/2012 |

(Continued)

OTHER PUBLICATIONS

Yonezawa et al. Layered Nanocomposite of Close-Packed Gold Nanoparticles and TiO2 Gel Layers. Chem. Mater. (1999), 11, 33-35. (Year: 1999).*

(Continued)

*Primary Examiner* — Sean C. Barron
(74) *Attorney, Agent, or Firm* — Squire Patton Boggs (US) LLP (57) ABSTRACT

A cell culture substrate includes: a first layer that includes a first gel in which gold nanoparticles dispersed; and a second layer that includes a second gel in which the gold nanoparticles are not present or are present in a lower concentration in comparison with the first layer.

3 Claims, 9 Drawing Sheets

(52) U.S. Cl.
CPC ...... *C12N 2531/00* (2013.01); *C12N 2533/54* (2013.01); *C12N 2539/10* (2013.01)

(58) Field of Classification Search
CPC .......... C12N 2533/54; C12N 2539/10; C12M 25/16; C12M 23/20; C12M 1/00
See application file for complete search history.

(56) References Cited

FOREIGN PATENT DOCUMENTS

| JP | 2013-233101 A | 11/2013 |
|---|---|---|
| JP | 2017-000113 A | 1/2017 |
| WO | WO 2018-003443 A1 | 1/2018 |

OTHER PUBLICATIONS

Ozasa et al. Contact angle and biocompatibility of sol-gel prepared TiO2 thin films for their use as semiconductor-based cell-viability sensorsSurface and Interface Analysis (2008), 40, 579-583. (Year: 2008).*
Chernak et al. High-Aspect-Ratio Gold Nanorods: Their Synthesis and Application to Image Cell-Induced Strain Fields in Collagen Films. Chapter 1 in Methods in Molecular Biology (2013), 1026, 1-20. (Year: 2013).*
Thermo Scientific Nunc Chamber Slides, Chambered Coverglass, and Flasks on Slides. (2012), 3 pages, BRLSPCHAMBERS 0412. (Year: 2012).*
Lee et al. Micro glass ball embedded gels to study cell mechanobiological responses to substrate curvatures. Review of Scientific Instruments (2012), 83, 094302, 7 pages. (Year: 2012).*
Hribar et al. Three-dimensional direct cell patterning in collagen hydrogels with near-infrared femtosecond laser. Scientific Reports (2015), 5(17203), 1-7. (Year: 2015).*
EPO Communication dated Oct. 12, 2020 forwarding the extended European Search Report for European Patent Application No. 18739383.0, 9 pages.
Kojima, et al: "Visible laser-induced in situ cell detachment from gold nanoparticle-embedded collagen gel", Macromolecular Bioscience; Dec. 2, 2016; vol. 17, No. 5, pp. 1-4; XP055450579.
Nakajima, et al: "Visible light-responsive cell scaffolds with bilayer structures for single cell separation", Research on Chemical Intermediates; Jan. 19, 2018; vol. 44, No. 8, pp. 4745-4754; XP036553986.
Xing, et al: "Regulating cell apoptosis on layer-by-layer assembled multilayers of photosensitizer-couple polypeptides and gold nanoparticles", Scientific Reports; May 1, 2016; vol. 6, No. 1, pp. 1-9; XP055734199.
International Search Report dated Apr. 10, 2018 for Application No. PCT/JP2018/000529, English translation, 1 page.
Written Opinion of the International Searching Authority dated Apr. 10, 2018 for Application No. PCT/JP2018/000529, English translation, 10 pages.
Communication Pursuant to Article 94(3) dated Jul. 22, 2021 issued for European Patent Application No. 18739383.0, 6 pages.
Communication Pursuant to Article 94(3) dated Feb. 28, 2022 issued for European Patent Application No. 18739383.0, 7 pages.
Notice of Reasons For Rejection dated Mar. 15, 2022 for Japanese Patent Application No. 2018-561419, with English translation, 15 pages.
Communication Pursuant to Article 94(3) dated Jan. 13, 2023 issued for European Patent Application No. 18739383.0; 4 pages.

* cited by examiner

CELL CULTURE SUBSTRATE, CULTURE VESSEL, METHOD FOR PRODUCING CELL CULTURE VESSEL, METHOD FOR ACQUIRING CELLS AND METHOD FOR CULTURING CELLS

This application is a continuation application of International Application No. PCT/JP2018/000529 filed Jan. 11, 2018.
The disclosure of the following priority application is herein incorporated by reference:
Japanese Patent Application No. 2017-003427 filed Jan. 12, 2017; and
International Application No. PCT/JP2018/000529 filed Jan. 11, 2018.

TECHNICAL FIELD

The present invention relates to a cell culture substrate, a culture vessel, a method for producing a cell culture vessel, a method for obtaining cells and a method for culturing cells.

BACKGROUND ART

There is a method proposed as the prior art in which cells are cultured on a culture substrate containing, for instance, a thermosensitive polymer, so as to obtain cells having been cultured on the culture substrate with a high level of efficiency by inducing temperature changes to advantage (see PTL 1).

CITATION LIST

Patent Literature

PTL 1: Japanese Laid Open Patent Publication No. H11-349643

SUMMARY OF INVENTION

According to the first aspect of the present invention, a cell culture substrate comprises: a first layer that includes a first gel in which gold nanoparticles dispersed; and a second layer that includes a second gel in which the gold nanoparticles are not present or are present in a lower concentration in comparison with the first layer.

According to the second aspect of the present invention, a culture vessel that includes a cell culture substrate wherein the substrate comprises: a first layer that includes a first gel in which gold nanoparticles dispersed; and a second layer that includes a second gel in which the gold nanoparticles are not present or are present in a lower concentration in comparison with the first layer.

According to the third aspect of the present invention, a method for producing a cell culture vessel, comprises the steps of: forming a first gel layer inside the cell culture vessel; and, above the first gel layer, forming a second gel layer in which gold nanoparticles dispersed, wherein: the first gel layer does not contain gold nanoparticles or contains gold nanoparticles in a lower concentration in comparison with the second gel layer.

According to the fourth aspect of the present invention, a method for obtaining a cell, comprised steps of: culturing a cell on a cell culture substrate that includes a first gel layer in which gold nanoparticles dispersed; and a second gel layer in which the gold nanoparticles are not present or are present in a lower concentration in comparison with the first gel layer; irradiating with light at least a portion of the first gel layer adjacent to at least one cell; and obtaining the at least one cell.

According to the fifth aspect of the present invention, a method for culturing a cell obtained by the method for obtaining a cell according to the fourth aspect.

DESCRIPTION OF EMBODIMENT

First Embodiment

The following is a description given in reference to drawings as needed, of the cell culture substrate, the culture vessel, the method for obtaining cells and the like according to an embodiment.

It is often necessary to efficiently isolate specific cells such as cells in which genetic material has been successfully introduced, among cells having been cultured on a cell culture substrate. During this process, a local change in the temperature may be induced at the cell culture substrate by radiating with light from an outside light source on a specific area as an aid in the isolation of specific cells, and in such a case, it is crucial to adjust the temperature in the irradiated area and the temperature in an area surrounding the irradiated area.

In general, a cell culture substrate enters a state of equilibrium as it wet-rises along the wall surface of a culture vessel at the interface with which a meniscus structure is formed due to a difference between the surface energy at the cell culture substrate and the surface energy at the wall surface of the culture vessel. For this reason, the thickness of the cell culture substrate, which is small in a central area and large in a peripheral area, is uneven. The degree of this unevenness in thickness increases, in relative terms, as the diameter of the culture vessel decreases and the quantity of the culture substrate decreases.

The inventors of the present invention discovered that this structural unevenness (i.e., the cell culture substrate having an uneven thickness) makes it difficult to control changes of temperature in the cell culture substrate during irradiation with light beam and ultimately makes it difficult to isolate individual cells from the cell culture substrate in the culture vessel.

The cell culture substrate according to the embodiment, which includes a plurality of gel layers, enables optimal adjustment and the like of temperature conditions since a first layer 10, to be explained later, achieves a thickness that is, on the whole, uniform within a plane of the culture vessel.

Figure 1A:
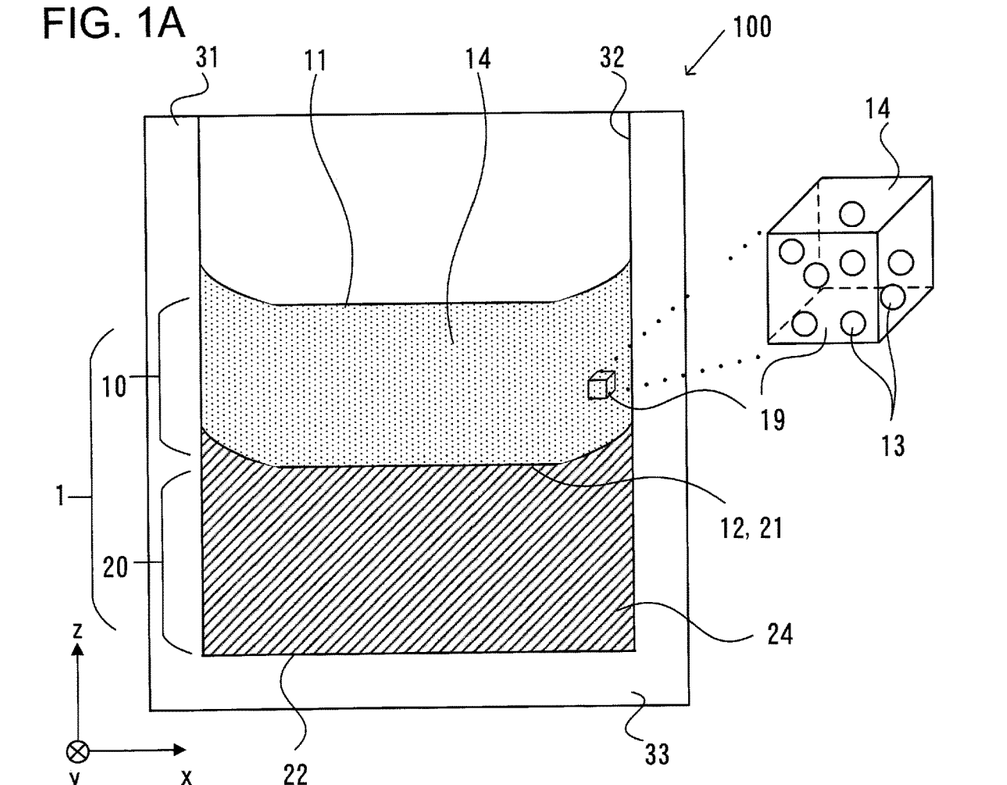
FIG. 1A shows a conceptual diagram illustrating a structure in a sectional view of the cell culture substrate according to an embodiment.
Figure 1B:
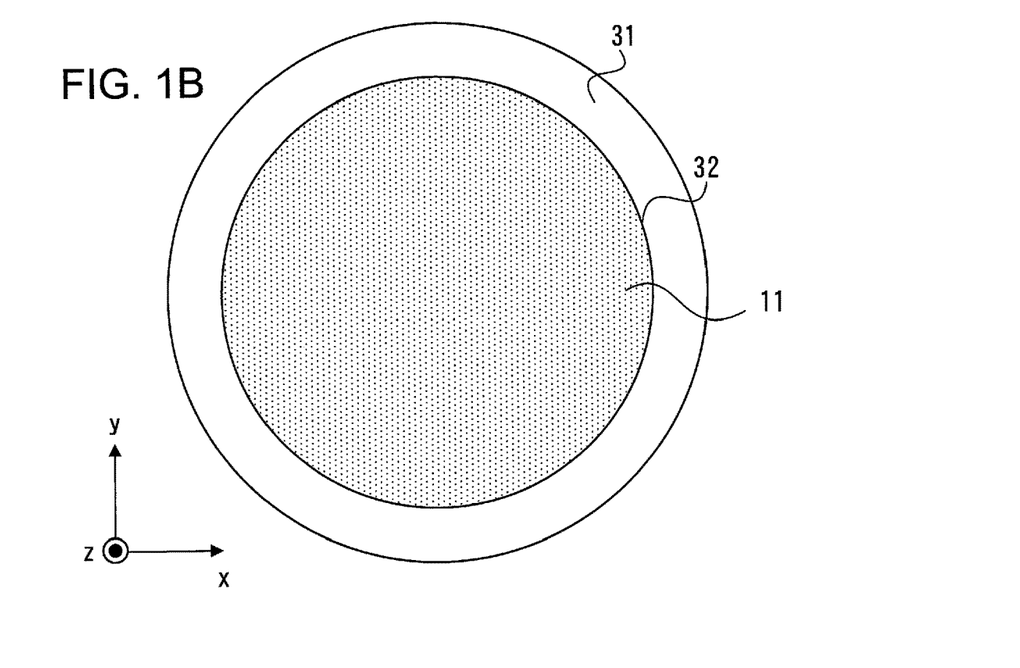
FIG. 1B shows a conceptual diagram illustrating a structure in a top view of the cell culture substrate according to the embodiment.

FIG. 1 provides conceptual diagrams illustrating the structure of a culture vessel 100 that includes a cell culture substrate 1 according to the embodiment, with FIG. 1A presenting a sectional view taken along the central axis of a cell placing surface 11 and FIG. 1B presenting a top view. The culture vessel 100 includes the cell culture substrate 1, a sidewall 31, an opening portion 32 and a bottom portion 33. The cell culture substrate 1 includes the first layer 10 and a second layer 20. The first layer 10 and the second layer 20 are each constituted primarily of a gel. The first layer 10 includes a first gel 14 in which gold nanoparticles 13 are dispersed. The second layer 20 includes a second gel 24 in which no gold nanoparticles 13 are present or in which gold nanoparticles 13 are dispersed with a lower concentration level than the concentration level of the gold nanoparticles 13 in the first gel 14. The gold nanoparticles 13 are shown in schematic presentation by enlarging a micro volume element 19 inside the first layer 10. The gold nanoparticles 13 are shown by enlarging a micro-volume element 19 inside the first layer 10 in a schematic presentation.

While the culture vessel 100 and the cell culture substrate 1, in the embodiment, both assume a substantially cylindrical shape and constitute part of a "well plate", they may assume shapes other than a cylindrical shape.

It is desirable that the size of the gold nanoparticles 13 be set so as to achieve a high photothermal conversion efficiency and in particular, it is desirable that their size be set so as to induce an absorption by surface plasmon resonance (SPR). It is desirable that the mean volume diameter of gold nanoparticles 13, measured by using a laser diffraction particle size analyzer, be equal to or greater than 1 nm and less than 200 nm, it is more desirable that it be equal to or greater than 10 nm and less then 100 nm and it is still more desirable that it be equal to or greater than 30 nm and less than 70 nm. It is desirable that the concentration of the gold nanoparticles 13 in the first gel 14 be equal to or greater than 100 μM and less than 1000 μM and it is more desirable that it be equal to or greater than 200 μM and equal to or less than 500 μM. When the concentration of gold nanoparticles 13 is low, less heat is generated at the gold nanoparticles 13. Under such circumstances, the cell scaffold will not readily be collapsed and the success rate for cell detachment will be lowered. When, on the other hand, the concentration of gold nanoparticles 13 is high, greater localized temperature increases occur, which will make temperature control difficult and will also lead to a greater extent of damage to the cells.

It is to be noted that the gold nanoparticles 13 in the gel may be stabilized to a higher degree with a protective agent by, for instance, distributing them in dendrimer or by having them modified with molecules having an affinity to the gel.

The first layer 10 includes the placing surface 11 on which cells being cultured are placed, and a lower surface 12 that contacts an upper surface 21 of the second layer 20. The second layer 20 is formed so as to come into contact with a bottom surface 22 of the opening portion 32 of the culture vessel 100. Unless specifically noted, the embodiment will be described by assuming that a Z axis runs along a direction perpendicular to the placing surface 11 with an X axis and a Y axis that runs perpendicular to the X axis, both extending perpendicular to the Z axis, as indicated in the figure. In addition, the direction along which the Z axis extends may be otherwise referred to as "up/down" or "up/down direction" in the following description of the embodiment.

It is to be noted that while the cell culture substrate 1 according to the embodiment includes two layers, i.e., the first gel 14 and the second gel 24, the present invention may be adopted in a cell culture substrate that includes a greater number of layers.

The first gel 14 becomes denatured as the temperature rises from room temperature to a predetermined level. The term "denaturation" used in the description of the embodiment refers to a structural change in the first gel 14 that occurs as the temperature increases, and results in easier cell detachment. The first gel 14 constituted with, for instance, a collagen gel or a gelatin gel, may become denatured as a change occurs in the secondary or tertiary structure of, for instance, collagen protein resulting in solation, agglomeration, decomposition into smaller molecules or the like. It is desirable that the temperature at which the first gel 14 becomes denatured be 60° C. or lower, it is more desirable that the temperature be 50° C. or lower and it is even more desirable that the temperature be 40° C. or lower. While no particular limitations are imposed with respect to the material to constitute the first gel 14, as long as it allows cells to be obtained through detachment, as will be explained later, it is desirable that the first gel 14 be constituted of a material that can be used in combination with another polymer material and it is more desirable to use a collagen gel or a gelatin gel to constitute the first gel 14. While no particular limitations are imposed with respect to the second gel 24, it is desirable that the second gel 24 be a dispersoid identical to the first gel 14.

The bottom portion 33 of the culture vessel 100 may have optical transparency. The culture vessel 100 may be formed in any shape as long as the technical features of the culture vessel 100 according to the embodiment remain intact.

It is to be noted that the bottom portion 33 and the second gel 24 in the culture vessel 100 included in a cell acquisition system 1000 configured so as to be irradiated with laser light from the side where the placing surface 11 is located toward the first layer 10, as will be described later, do not need to have optical transparency.

Figure 2:
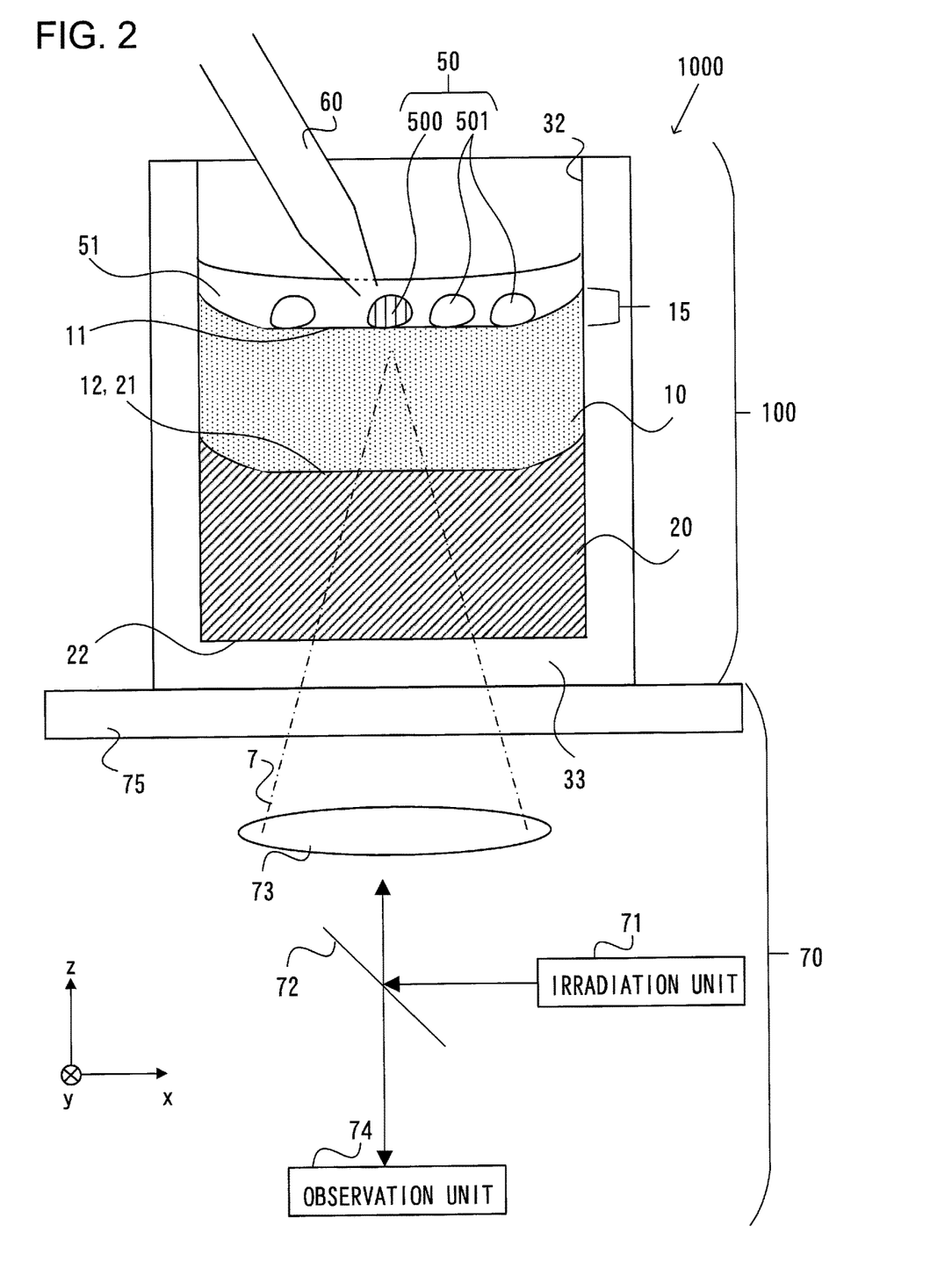
FIG. 2 shows a conceptual diagram illustrating the structure of a cell acquisition system that includes the cell culture substrate according to the embodiment.

FIG. 2 is a conceptual diagram of the cell acquisition system 1000, in which cells are obtained by using the cell culture substrate 1. The cell acquisition system 1000 includes the culture vessel 100 and an inverted microscope 70. In the culture vessel 100, cells 50 are cultured in a buffer solution 51 on the placing surface 11 of the first layer 10.

Among the cells 50 cultured on the cell culture substrate 1, a cell to be isolated and obtained will be referred to as a select cell 500 and other cells will be referred to as non-select cells 501. While no particular limitations are imposed with respect to a state of the select cell 500, the select cell ideally will be a cell carrying an optimally modified gene or the like and judged to manifest specific characteristics by a decision-making means such as a reporter gene, a cell in which initialization or optimal differentiation has been induced to manifest characteristics that are structurally recognizable, or the like.

It is to be noted that the select cell 500 may be a single cell 50 as described above, or it may be a plurality of cells 50 or a colony that is formed with a plurality of cells 50.

The inverted microscope 70 includes an irradiation unit 71, a dichroic mirror 72, a lens system 73, an observation unit 74 and a support stage 75.

It is to be noted that if the potentially adverse effect of the cells 50 directly irradiated with light or the like is not an issue, the cell acquisition system 1000 may be configured by using an upright microscope.

The irradiation unit 71 emits laser light. The wavelength of the laser light emitted from the irradiation unit 71 is set within a wavelength range over which the gold nanoparticles 13 exhibit photothermal conversion and it is particularly desirable to set it within the wavelength range over which absorption occurs by surface plasmon resonance (SPR). The laser light with which irradiates the first gel 14 will be such that its wavelength and energy do not seriously damage cells when it irradiates them. It is desirable that the wavelength of the laser light emitted from the irradiation unit 71 be equal to or greater than 400 nm and less than 1200 nm, and it is more desirable that it be equal to or greater than 450 nm and less then 900 nm, e.g., it may be set to 532 nm. It is desirable that the output of laser light entering the culture vessel 100 be equal to or greater than 0.1 mW and less than 1000 mW, and it is more desirable that the laser light output be equal to or greater than 0.4 mW and less than 100 mW. The wavelength and the energy of the laser light are adjusted as needed so as to induce a temperature increase and denaturation at the first gel 14 with high efficiency without damaging the cells. The light emitted from the irradiation unit 71 enters the dichroic mirror 72.

It is to be noted that as long as an area around the select cell 500 can be selectively irradiated, the light emitted from the irradiation unit 71 does not need to be laser light and instead monochromatic light that is not coherent, or light within a predetermined wavelength range may be adopted.

The laser light from the radiation unit 71 is reflected at the dichroic mirror 72 and, in addition, visible light from the culture vessel 100, transmitted through the dichroic mirror 72, exits the dichroic mirror 72 to travel toward the observation unit 74. The direction of the laser light reflected at the dichroic mirror 72 is adjusted via a galvanometer mirror or the like (not shown) so that an optimal position is irradiated with the laser light, and the laser light is transmitted through the lens system 73 to enter the culture vessel 100. The laser light having entered the culture vessel 100 is transmitted through the bottom portion 33 of the culture vessel 100 and the second layer 20, and then it becomes converged in the first layer 100 at a predetermined position near the select cell 500. In FIG. 2, converging laser light 7 is schematically indicated by using one-point chain lines.

It is to be noted that as long as the laser light 7 is made to converge at a desired position, no particular limitations are imposed with respect to the structure of the irradiation optical system for the laser light 7.

It is desirable that the laser light 7 be made to converge in the first layer at a position below the select cell 500, as close as possible to the select cell 500 without damaging the select cell 500, and the convergence position may be set based upon, for instance, the spot diameter of the laser light 7, a PSF (point spread function), a PSF-based parameter or the like. It is desirable that the laser light 7 converge in the first layer 10 directly below the select cell 500 within a depth range of less than 100 µm or within a radius of less than 100 µm from the cell body of the select cell 500. In addition, if cell damage is not an issue, the convergence position may be set at the select cell 500.

As the laser light 7 emitted from the irradiation unit 71 undergoes photothermal conversion at the gold nanoparticles 13, causing denaturation in the gel located near the position at which the laser light 7 converges, the physical or chemical characteristics of the gel functioning as the scaffold of the select cell 500 or of the surrounding environment change, which, in turn, reduces the force with which the select cell 500 adheres to the placing surface 11. Accordingly, the select cell 500 alone can be extracted by suctioning with a pipette 60.

It is to be noted that no particular limitations are imposed with respect to the method for physically obtaining the cell, and the cell may be extracted by, for instance, causing a perfusion of the buffer solution 51 on the placing surface 11 instead of using a pipette 60.

The observation unit 74, which includes an eyepiece lens and the like, enables the user to observe visible light originating from the culture vessel 100 irradiated with illuminating light (not shown). The user, looking at the visible light from the culture vessel 100, is able to set the culture vessel 100 to the optimal position and the like by, for instance, moving the support stage 75.

It is to be noted that an alternative structure in which an image of the culture vessel 100, obtained through laser scanning by using a laser light source different from the irradiation optical system for the laser light 7 and a galvanometer mirror, is brought up on display on a display device (not shown) may be adopted.

The support stage 75 supports the culture vessel 100. The support stage 75 is allowed to move along the X direction, the Y direction and the Z direction via a moving mechanism (not shown) and thus, the position of the culture vessel 100 can be adjusted so that it takes a desired position. The support stage 75, which includes glass with a transparent heat generation element formed therein, allows the laser light 7 to be transmitted through to the bottom portion 33 of the culture vessel 100 and the temperature of the entire culture vessel 100 is controlled via the support stage 75.

It is to be noted that depending upon the size, the structure and the like of the culture vessel 100, a support stage 75 having an opening portion, located in an area forming a light path of the laser light 7, may be utilized.

The cell culture substrate 1 according to the embodiment includes a plurality of gel layers so that the first layer 10, i.e., a heat generation layer, achieves a thickness that is, on the whole, approximately uniform within a plane. As a result, irradiation conditions with the laser light 7 can be adjusted with better ease, which, in turn, makes it possible to facilitate isolation of a cell even when the irradiation area is altered.

Figure 3:
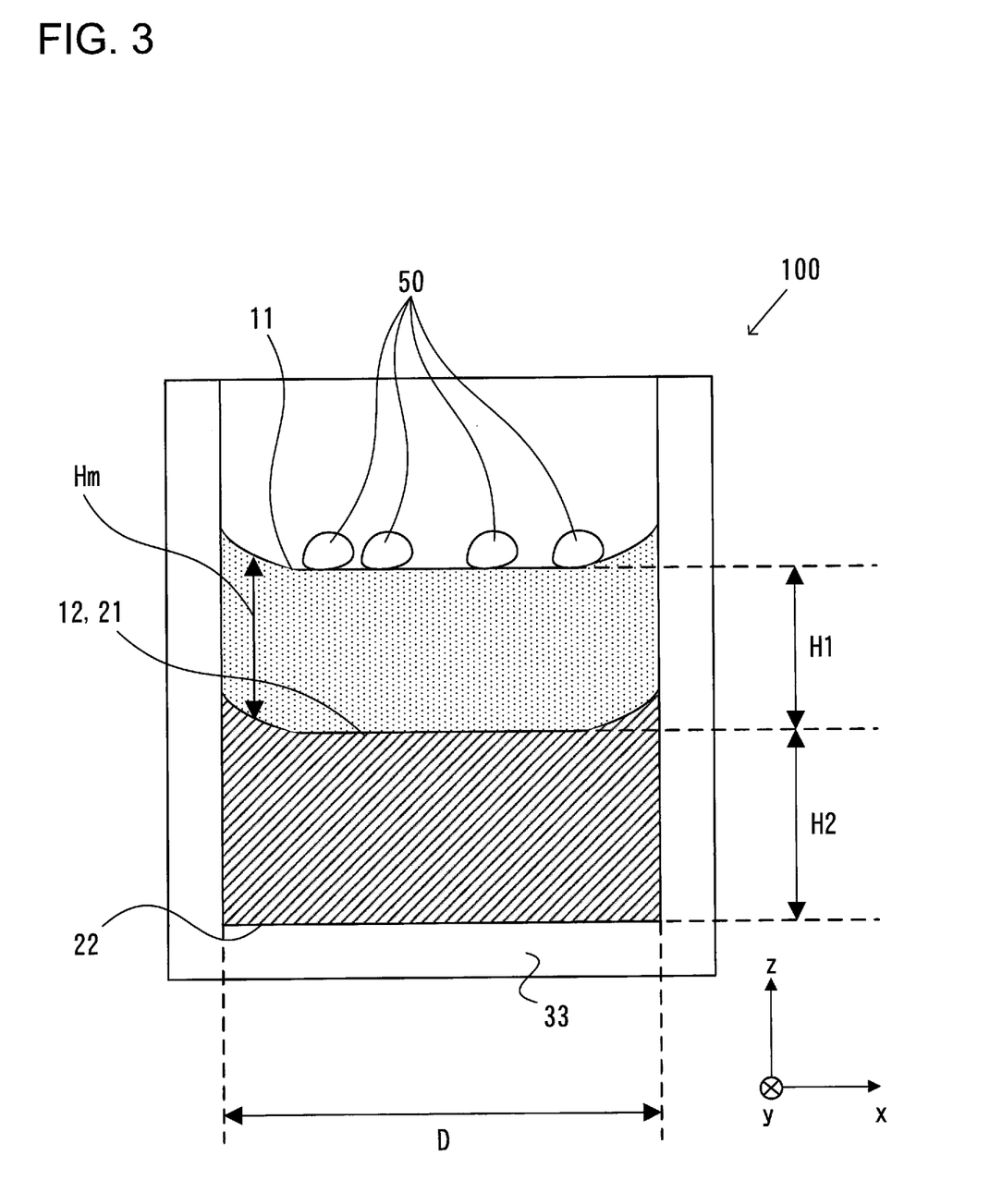
FIG. 3 shows a conceptual diagram illustrating the structure of the cell culture substrate according to the embodiment.

FIG. 3 is a sectional view of the culture vessel 100 with respect to an XZ plane passing through the central axis thereof.

It is desirable that a thickness H2 of the second layer 20 in the cell culture substrate 1 according to the embodiment be equal to or greater than 0.8 mm, it is more desirable that it be equal to or greater than 0.8 mm and equal to or less than 1.7 mm and it is even more desirable that it be equal to or greater than 0.8 mm and equal to or less than 1.2 mm. If the thickness H2 of the second layer 20 is too small, it will be difficult to form the first layer 10 and/or the second layer 20 as a uniform or flat layer. On the other hand, if the thickness H2 of the second layer is too large, light will have been weakened before reaching the first gel 14 in the first layer 10, to result in less heat being generated at the gold nanoparticles 13 in the vicinity of the cells 50, which, in turn, will make it difficult to obtain a cell 50.

A thickness H1 of the first layer 10 and the thickness H2 of the second layer 20 are measured in a central area of the cell culture substrate 1, e.g., measured along the central axis.

No particular limitations are imposed with respect to the constitution of the second layer unless the first layer becomes the meniscus structure and the thickness thereof becomes non-uniform in the central area and the peripheral area. The second layer may be made up with a plurality of layers In such a case, it is desirable that the total thickness of the plurality of layers be equal to or greater than 0.8 mm. In addition, since the difference in the surface tension of the gels is bound to alter the meniscus structure, it is desirable to select gel materials for the first layer 10 and the second layer 20 that achieve surface tensions (mN/m) close to each other and it is even more desirable that the first layer 10 and the second layer 20 be constituted of the same gel material.

It is desirable that the ratio of the thickness H1 of the first layer 10 to the thickness H2 of the second layer 20 (hereafter will be referred to as a thickness ratio H1/H2) be equal to or greater than 0.5, it is more desirable that the thickness ratio be equal to or greater than 1.0 and it is even more desirable that the thickness ratio be equal to or greater than 2.0. In addition, it is desirable that the value (the thickness ratio H1/H2) be equal to or less than 5, it is more desirable that the value be equal to or less than 4 and it is even more desirable that the value be equal to or less than 3. An excessively small value for the thickness ratio H1/H2 may be attributable to the first layer 10, formed with a very small thickness, and in such a case, it will be difficult to form the first gel 14 as a uniform or flat layer. An excessively small value for the thickness ratio H1/H2 may be attributable to the second layer 20, formed with a very large thickness, and in such a case, only weak light will reach the first gel 14 in the first layer 10, as explained earlier, to result in less heat being generated at the gold nanoparticles 13 in the vicinity of the cells 15, making it difficult to obtain a cell 50. When the first gel 14 is formed as a uniform or flat layer, the thickness H1 measured in a central area of the first gel 14 and a thickness Hm of the first gel 14 measured near the side wall will be equal to each other or close to each other.

Figure 4A:
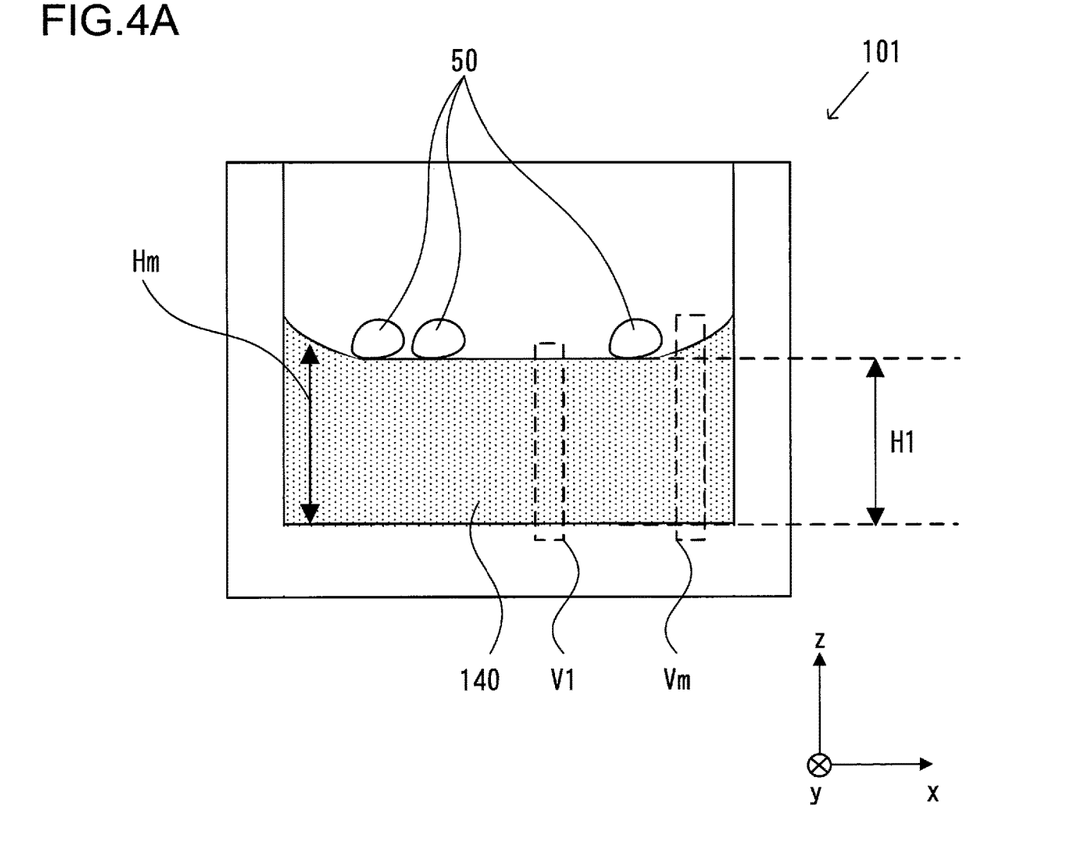
FIG. 4A shows a sectional view of a cell culture substrate of the prior art.

FIG. 4 presents conceptual diagrams (sectional views), illustrating how a thickness (H1) in a central area of the heat generation layer and a thickness (Hm) of the heat generation layer, measured near the side wall, affect the amount of heat generated at a cell culture substrate of the prior art. FIG. 4A presents an example of a cell culture vessel 101 of the prior art with a single layer gel 140 constituting the cell culture substrate. The thickness H1 of the gel 140 assuming a meniscus shape, measured in a central area, is different from the thickness Hm measured near the side wall.

Figure 4B:
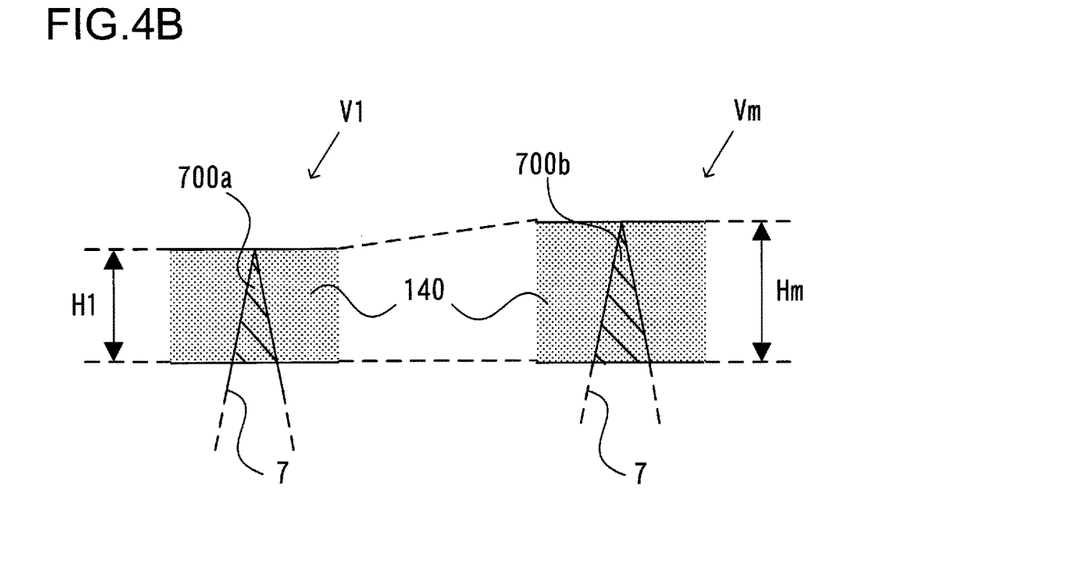
FIG. 4B shows an enlargement for comparison showing the areas enclosed by the dotted lines in FIG. 4A.

FIG. 4B shows an area V1 and an area Vm, each enclosed by a dotted line in FIG. 4 A, in an enlargement so as to facilitate comparison. In the gel 140 assuming different thicknesses over its central area and the area near the side wall in the culture vessel 101, the volume of an irradiation region 700a (the shaded region in V1), which is irradiated with the laser light 7 over the central area will be different from the volume of an irradiation region 700b (the shaded region in Vm), which is irradiated with the laser light 7 near the side wall. This means that different amounts of heat will be generated with the laser light 7 in the central area and in the area near the side wall at the gel 140. In addition, since a cell 50 can be detached alive only over a limited temperature range at the gel containing gold nanoparticles, control under which the temperature is increased for purposes of detaching the cell 50 will depend upon the thickness of the heat generation layer as well as on the laser intensity. Accordingly, control for temperature increase at the gel 140 with an uneven thickness is bound to require a considerable length of time and consequently, cells 50 can be obtained with high efficiency on the placing surface 11 only over a limited range.

Figure 5A:
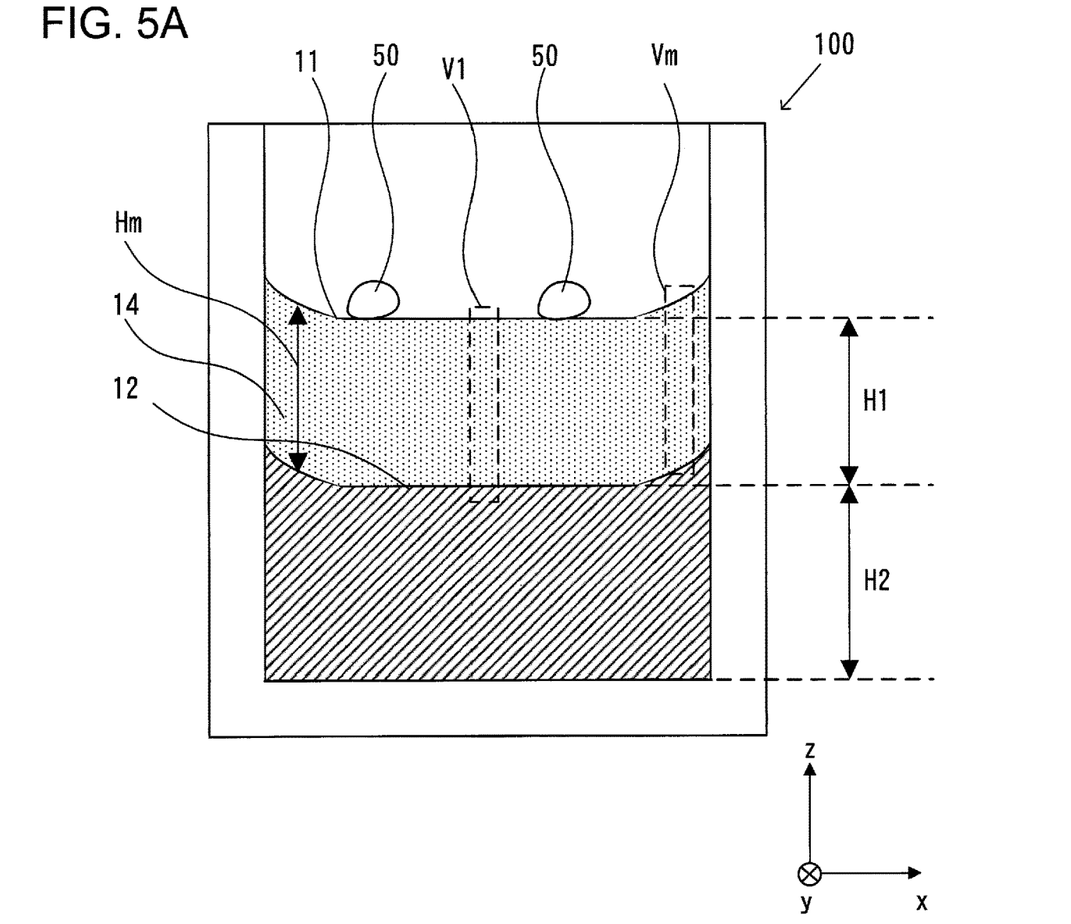
FIG. 5A shows a sectional view of the cell culture substrate according to the embodiment.

FIG. 5 presents conceptual diagrams (sectional views) illustrating how the thickness (H1) in a central area of the first gel 14 according to the embodiment, and the thickness (Hm) of the first gel 14 according to the embodiment measured near the side wall, affect the amount of heat generated at the culture vessel 100 according to the embodiment. In FIG. 5A, an area V1, which includes part of the bottom surface 12 of the first gel 14 and part of the placing surface 11 of the first gel 14, located at the center of the first gel 14 and an area Vm, which includes part of the bottom surface 12 of the first gel 14 and part of the placing surface 11 of the first gel 14, located in the first gel 14 near the side wall, are each enclosed by a dotted line.

Figure 5B:
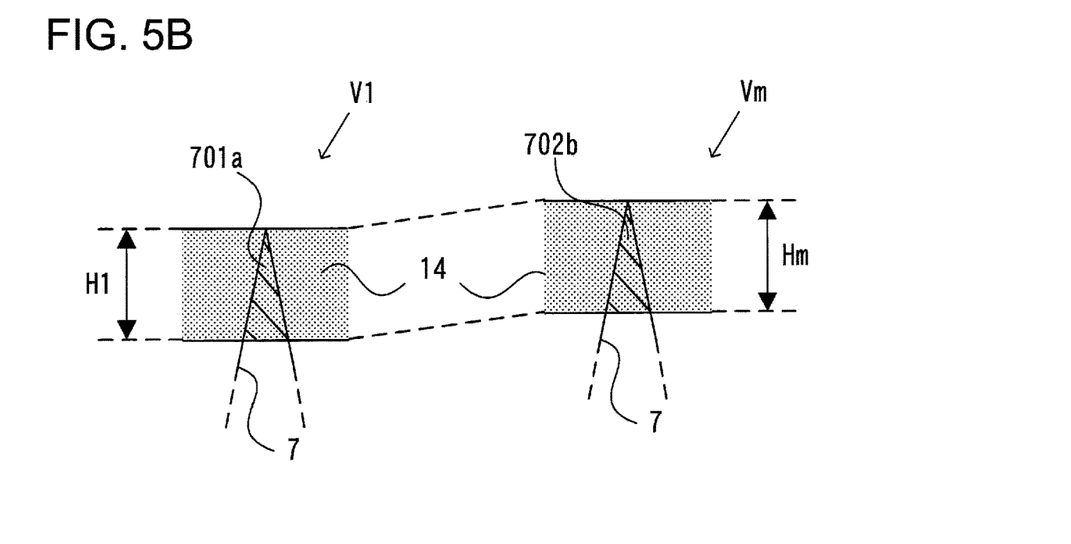
FIG. 5B shows an enlargement for comparison showing the areas enclosed by dotted lines in FIG. 5A.

FIG. 5B shows the area V1 and the area Vm, each enclosed by the dotted line in FIG. 5A, in an enlargement so as to facilitate comparison. In the culture vessel 100 according to the embodiment, the thicknesses H1 and Hm measured at the central area and at the area near the side wall are substantially equal to each other, and thus, the volume of an irradiation region 701a (the shaded region in V1), which is irradiated with the laser light 7 in the central area, and the volume of an irradiation region 701b (the shaded region in Vm), which is irradiated with the laser light 7 near the side wall, too, are substantially equal to each other. This means that the amount of heat generated with the laser light 7 in the central area of the first gel 14 and the amount of heat generated with the laser light 7 in the area of the first gel 14 near the side wall are substantially equal to each other. In the cell culture substrate 1 according to the embodiment, the first gel 14 is formed so as to achieve a uniform thickness from the central area through the peripheral area, making it possible to obtain cells 50 with high efficiency from a wider area on the placing surface 11. Since the extent of inconsistency with which the temperature increases depending upon the position of the target cell 50 to be detached is reduced, adjustment of the laser energy, the irradiation time and the like at various irradiation positions is facilitated or the need for such adjustment will be eliminated altogether.

An excessively large value taken for the thickness ratio H1/H2 may be attributable to the first layer 10 formed with a very large thickness, and in such a case, scattering of light by the gold nanoparticles 13 will weaken the light reaching a point directly underneath a cell, to result in difficulty in cell acquisition, or it may be attributable to the second layer 20 formed with a very small thickness and in such a case, it will be difficult to form the second layer 20 as a uniform or flat layer.

At the cell culture substrate of the prior art constituted with a heat generation layer alone, its meniscus structure with a small gel thickness in the central area of the cell culture substrate will make it difficult to adjust the irradiation time and the level of energy of the laser light 7, which is bound to result in accumulation of heat by the gold nanoparticles and in an extreme case, may result in an unexpected situation such as agglomeration of the gold nanoparticles, gel blackening or the like. In the cell culture substrate 1 according to the embodiment, which includes the second layer 20, the first layer 10 is allowed to achieve, on the whole, an approximately uniform thickness, which assures better ease of temperature adjustment. In addition, issues such as the gel blackening mentioned above can be prevented as the temperature in a central area of the first layer 10 can be adjusted through thermal diffusion and the like. The problem of gel blackening becomes particularly pronounced when an inner diameter D (see FIG. 3) of the culture vessel 100 or the maximum diameter of the first layer 10 measured at the placing surface 11 is small, since the meniscus structure 15 in the first layer 10 is bound to greatly affect the thickness of the first layer 10 in a central area under such circumstances. Accordingly, it is desirable, with respect to the cell culture substrate 1, that the inner diameter D of the culture vessel 100 be less than 10 cm so as to bring forth more marked benefit of an uniformly formed first layer 10, and it is more desirable that the inner diameter D be less than 5 cm and it is even more desirable that it be less than 2.5 cm. The inner diameter D is a diameter achieving the greatest length running along a direction perpendicular to the central axis (see FIG. 3).

Method for Producing the Cell Culture Substrate 1

Figure 6:
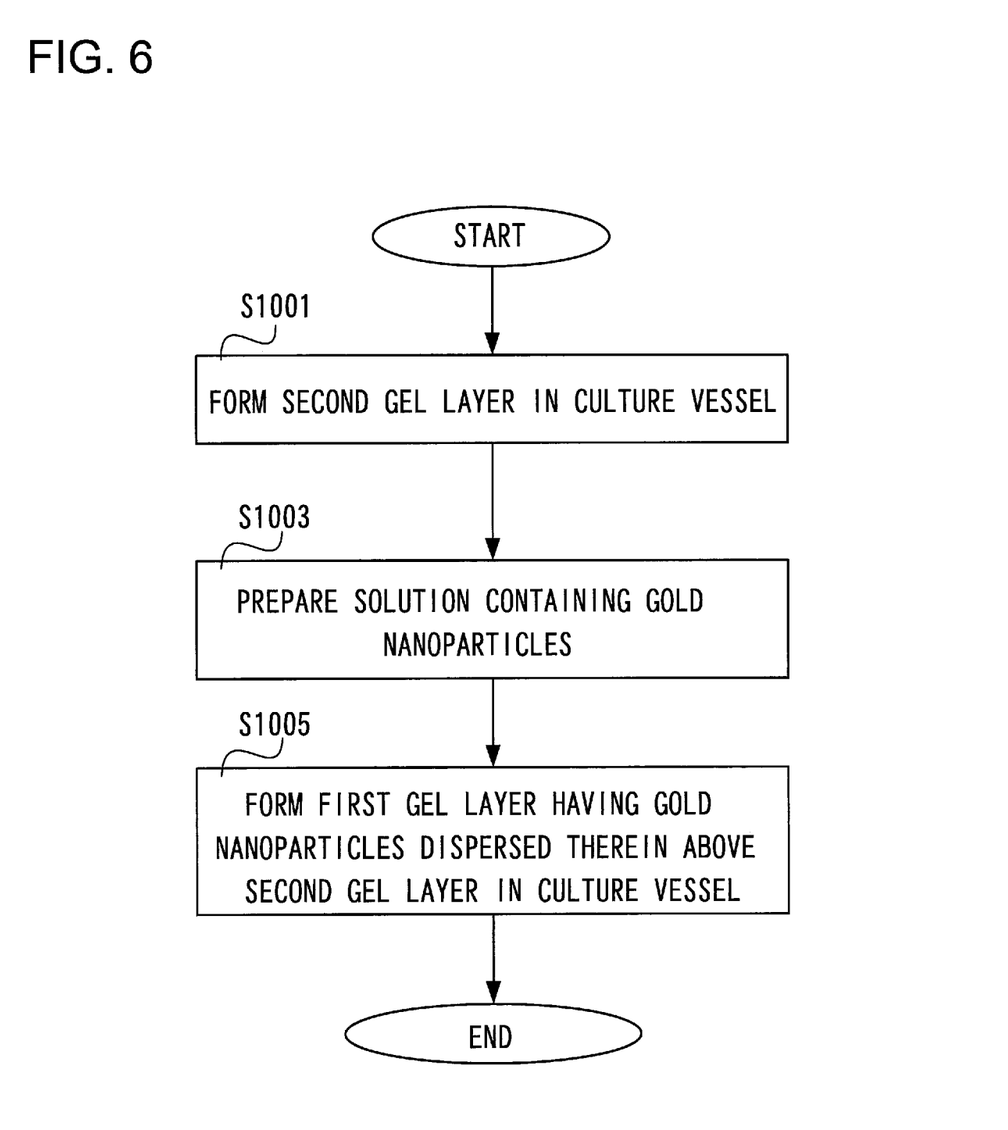
FIG. 6 shows a flowchart pertaining to a method for producing the cell culture substrate according to the embodiment.

FIG. 6 presents a flowchart pertaining to a method for producing the cell culture substrate 1 according to the embodiment. In step S1001, a layer made up with the second gel 24, constituted with a collagen gel or the like, is formed in the culture vessel 100. Once the processing in step S1001 is completed, the operation proceeds to step S1003.

In step S1003, a solution containing gold nanoparticles 13 achieving a predetermined mean volume diameter is prepared. Such a solution may be obtained by, for instance, growing seed nuclei constituted of gold in the presence of a reducing agent (ascorbic acid, hydroquinone, citric acid or the like) in a solution containing gold ions (e.g., $HAuCl_4$), as described in Japanese Laid Open Patent Publication No. 2013-233101. Once the processing in step S1003 is completed, the operation proceeds to step S1005.

It is to be noted that the order with which the processing in step S1001 and the processing in step S1003 are executed may be reversed as needed or they may be executed concurrently.

The mean volume diameter of the gold nanoparticles 13 can be measured with a laser diffraction particle size analyzer once the gold nanoparticles 13 have been prepared. However, a mean volume diameter may be obtained through a simpler method without utilizing a particle size analyzer, by capturing an image via a transmission electron microscope and calculating a mean volume diameter through measurement executed in conjunction with, for instance, an analysis software program.

In step S1005, a layer of the first gel 14 with gold nanoparticles 13 dispersed therein is formed above the layer of the second gel 24 inside the culture vessel 100. A mixed solution containing collagen and gold nanoparticles 13 is prepared by using the solution containing the gold nanoparticles 13 having been prepared in step S1003, the mixed solution is then poured onto the second gel and is allowed to stand in the culture vessel. When the mixed solution has set, the gold nanoparticles 13 are dispersed and embedded in the collagen gel. Once the processing in step S1005 is completed, the process ends.

Figure 7:
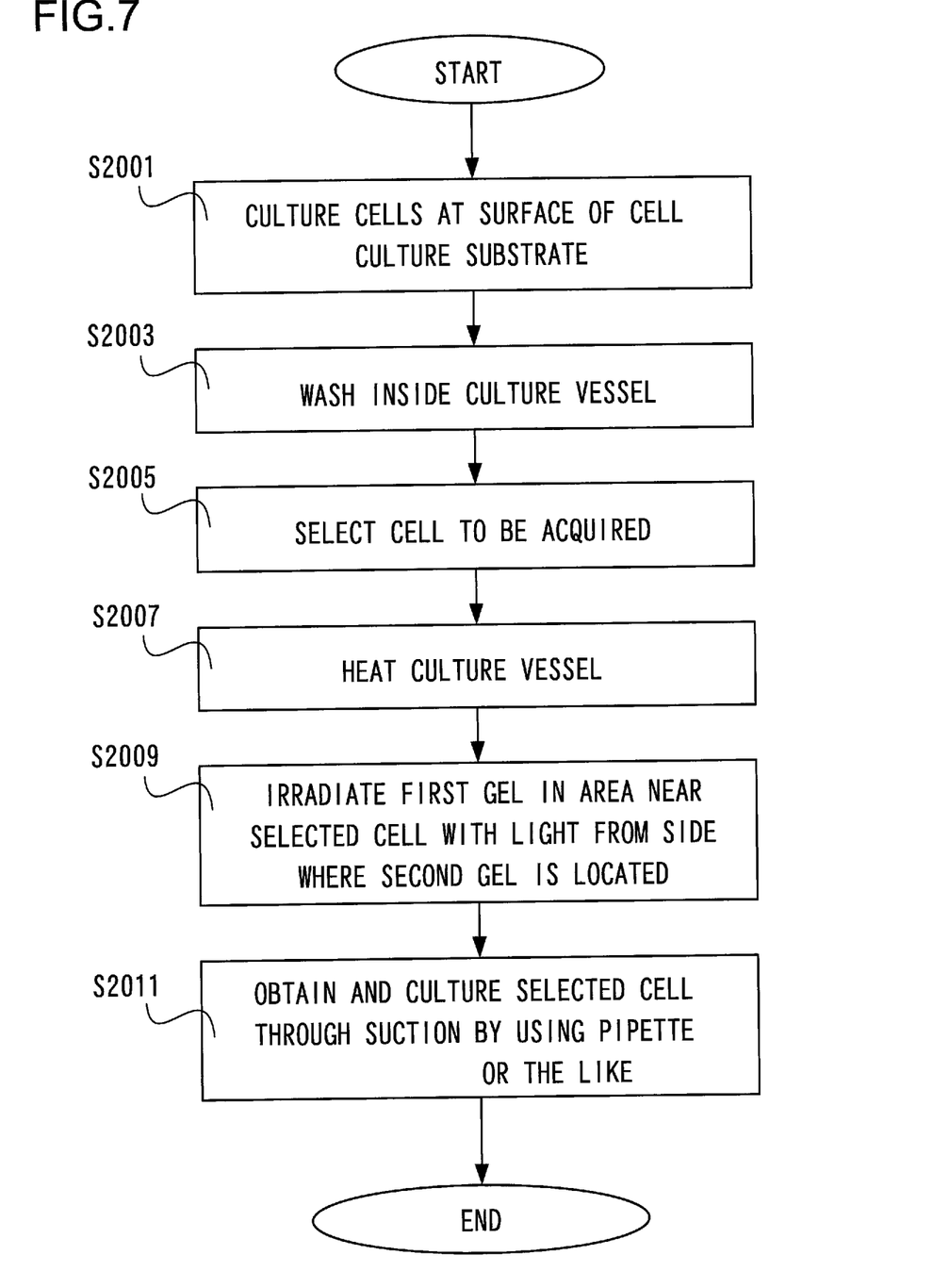
FIG. 7 is a flowchart pertaining to a method for obtaining cells by using the cell culture substrate according to the embodiment.

FIG. 7 presents a flowchart pertaining to a cell acquisition method and a production method, achieved in conjunction with the cell culture substrate 1 according to the embodiment. In step S2001, cells are cultured on the surface of the cell culture substrate 1, i.e., on the placing surface 11. Once the processing in step S2001 is completed, the operation proceeds to step S2003. In step S2003, the interior of the culture vessel 100 and in particular, the placing surface 11, is washed. Through the washing process executed by using PBS or the like, unwanted suspended matter, deposits and the like are removed.

In step S2005, a cell 50 (select cell 500) to be obtained, among the cells 50 having been cultured on the placing surface 11, is selected. A cell 50 manifesting a fluorescent protein, a cell 50 manifesting specific structural characteristics, or the like, is selected as required for specific applications. Once the processing in step S2005 is completed, the operation proceeds to step S2007. In step S2007, the temperature at the support stage 75 is adjusted to an optimal level and the culture vessel 100 is heated to a temperature lower than the temperature at which the entire first gel 14 undergoes denaturation. By raising the temperature of the culture vessel 100 before irradiation with the laser light 7, the irradiation time with laser light 7 can be reduced so as to reduce the risk of damage to the select cell 500.

In step 2009, laser light 7 forwarded from the side where the second layer 20 is located toward the convergence position set near the select cell 500 in the first layer 10. By irradiating with the laser light 7 from the side where the second layer 20 is located, it is ensured that no cell damage will be caused to the cells 50 by direct irradiation with the light. In addition, since no gold nanoparticles 13 are present in the second layer 20 or the concentration of gold nanoparticles in the second layer 20 is lower than that in the first layer 10, attenuation of the laser light 7 through interaction with gold nanoparticles 13 before it reaches a point near the select cell 500 can be prevented. Once the bond between the select cell 500 and the placing surface 11 has been weakened, the operation proceeds to step S2011.

In step S2011, the select cell 500 is obtained through suction by using a pipette 60 and cells are cultured again as needed. The select cell 500 having been obtained can be placed in another culture medium or the like for further culturing. Once the processing in step S2011 is completed, the process ends. It is to be noted that after the select cell 500 is obtained in step S2011, the operation may return to step S2005 to obtain another cell 50 as a select cell 500. In addition, the select cell having been obtained may be directly utilized in any of various applications such as clinical applications, research applications and industrial applications.

The following advantageous effects are achieved through the embodiment described above.

(1) The cell culture substrate 1 according to the embodiment includes a first layer 10 where a first gel 14 with gold nanoparticles 13 dispersed therein is present and a second layer 20 where a second gel 14 with no gold nanoparticles 13 dispersed therein or with gold nanoparticles 13 dispersed therein at a concentration lower than that in the first layer 10 or the first gel 14, is present. As a result, the first layer 10 to sustain a uniform thickness H1, which makes it possible to detach cells 50 with high efficiency over a wider range at the placing surface 11 of the first layer 10.

(2) In the cell culture substrate 1 according to the embodiment, the first layer 10 includes a placing surface 11 at which cells 50 being cultured are placed and a surface 12 that is in contact with the second layer 20. As a result, heat be directly diffused and conducted from the first layer 10 to the second layer 20 so as to prevent gel blackening.

(3) In the cell culture substrate 1 according to the embodiment, the first gel 14 becomes denatured when it is heated to a temperature equal to 60° C. or lower. As a result, localized denaturation can be easily induced in the first gel 14 through irradiating locally the first layer 10 with the light.

(4) In the cell culture substrate 1 according to the embodiment, the first gel 14 is constituted with a gelatin gel or a collagen gel. As a result, the first gel can be manufactured, handled and the like with ease.

(5) In the cell culture substrate 1 according to the embodiment, the second gel 24 is constituted of a gel material identical to the gel material constituting the first gel 14. As a result, production of the cell culture substrate 1 is facilitated and also, occurrence of laser light refraction or loss at the boundary surface separating the first gel 14 and the second gel 24 from each other can be reduced, while even better uniformity is assured with respect to the thickness of the first layer 10.

(6) In the cell culture substrate 1 according to the embodiment, the mean volume diameter of the gold nanoparticles 13 is equal to or greater than 2 nm and less than 200 nm and the concentration of gold nanoparticles 13 in the first layer 10 is equal to or greater than 100 µM and less than 1000 µM. As a result, photothermal conversion in the first gel 14 and denaturation of the first gel 14 are induced with high efficiency at the gold nanoparticles 13.

(7) The culture vessel 100 according to the embodiment includes the cell culture substrate 1 and thus, a select cell 500 among cells 50 having been cultured can be extracted with high efficiency without subjecting the cells 50 to any significant damage.

(8) The method for obtaining cells according to the embodiment comprises steps of; selecting a select cell 500 to be obtained from cells 50 having been cultured at the cell culture substrate 1, irradiating the first layer 10 in the cell culture substrate 1 with light and recovering the select cell 500. Since this method allows cells 50 to be detached with high efficiency over a wider area at the placing surface 11 of the first layer 10, a greater number of cells 50 having been cultured at the placing surface 11 can be obtained with a high level of efficiency.

(9) In the method for obtaining cells according to the embodiment, the first layer 10 is irradiated with the laser light 7 having been transmitted through the second layer 20. Thus, since a select cell 500 can be obtained without directly irradiating the cells with the laser light 7 and thus without causing any cell damage and since no gold nanoparticles 13 are present in the second gel 24 or the concentration of gold nanoparticles 13 in the second gel 24 is lower than that in the first gel 14, attenuation of the laser light 7 in the second gel 24 can be prevented.

The following variation is also within the scope of the present invention and may be adopted in combination with the embodiment described above. In the description of the variation provided below, parts having structures or functions similar to those according to the above-described embodiment will be assigned with the same reference signs so as to preclude the necessity for a repeated explanation.

Variation 1

While a cell to be isolated for acquisition is designated as a select cell 500 according to the embodiment described above, areas near non-select cells 501 other than the select cell 500 may be irradiated with the laser light 7 so as to selectively retain the select cell 500 by detaching and removing the non-select cells 501.

Figure 8:
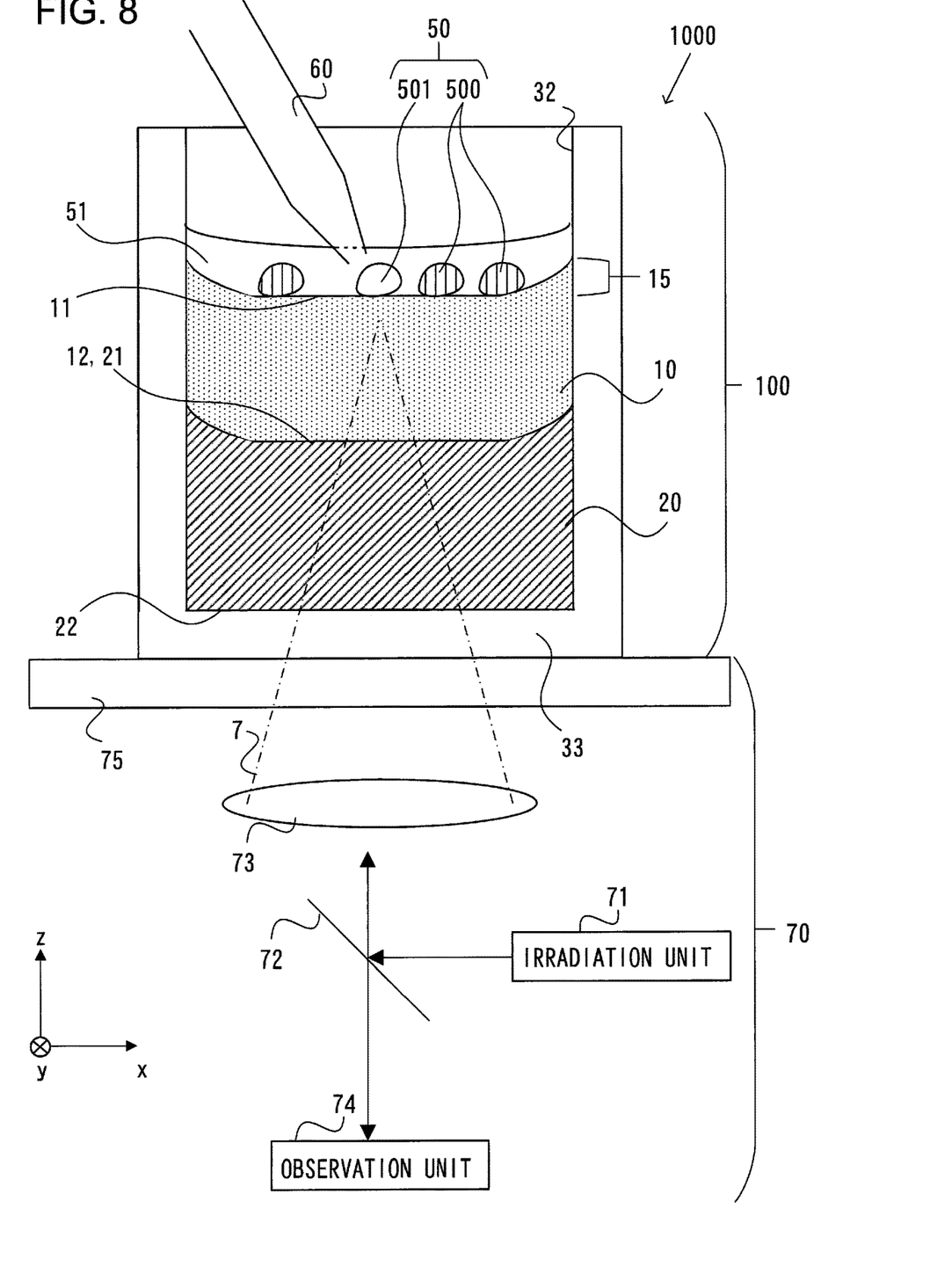
FIG. 8 shows a conceptual diagram illustrating the structure of a cell acquisition system that includes the cell culture substrate according to the embodiment.

FIG. 8 is a conceptual diagram of a cell acquisition system 1000 that may be adopted in conjunction with the cell acquisition method according to the variation. While the cell acquisition system 1000 is structurally similar to that described in reference to the embodiment, it is distinguishable in that an area near a non-select cell 501 is irradiated with the laser light 7.

Figure 9:
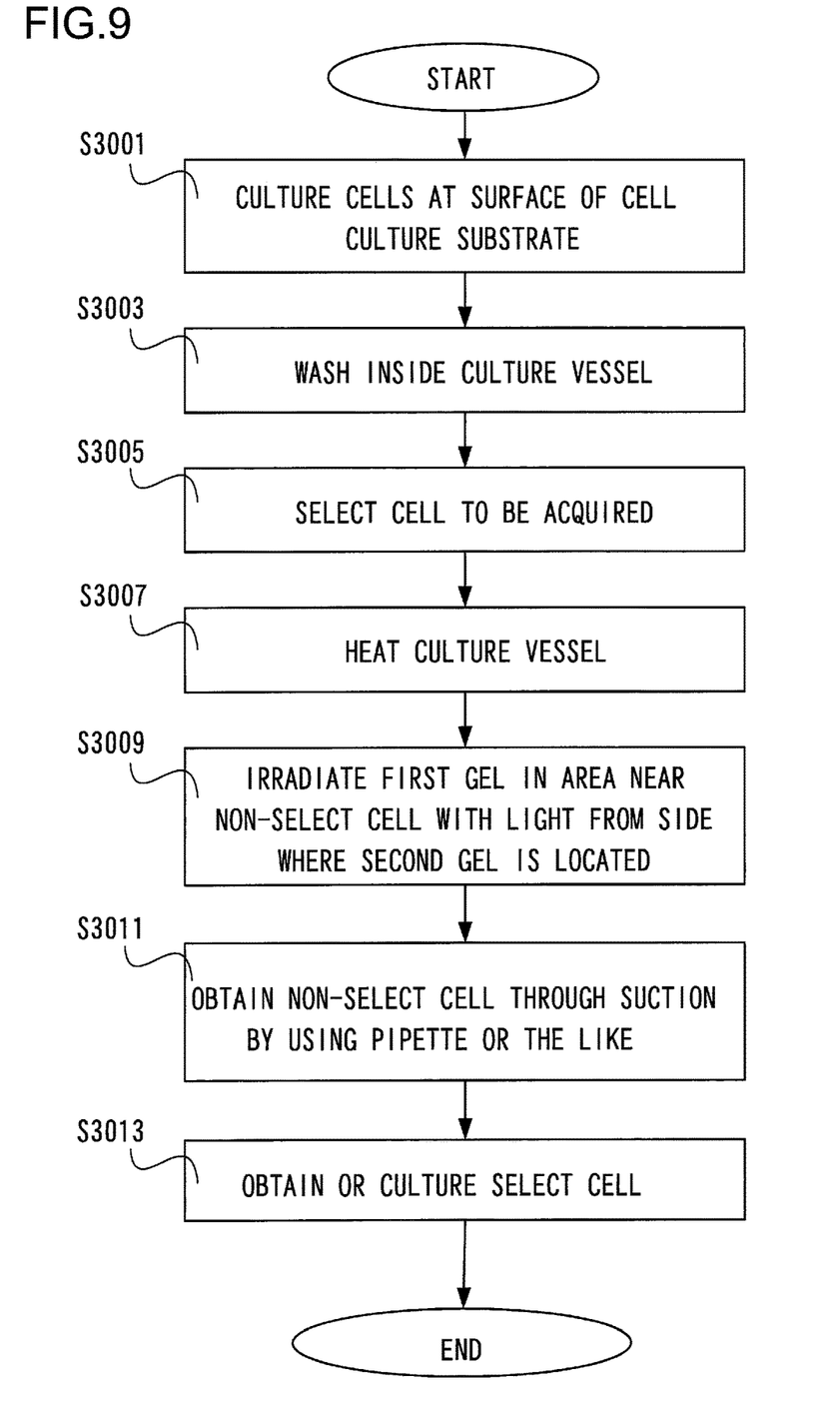
FIG. 9 shows a flowchart pertaining to a method for obtaining cells by using the cell culture substrate according to the embodiment.

FIG. 9 presents a flowchart pertaining to a cell acquisition method and a production method, achieved in conjunction with the cell culture substrate 1 according to the variation. In step S3001, cells are cultured on the surface of the cell culture substrate 1, i.e., on the placing surface 11. Once the processing in step S3001 is completed, the operation proceeds to step S3003. In step S3003, the interior of the culture vessel 100 and in particular, the placing surface 11, is washed. Through the washing process executed by using PBS or the like, unwanted suspended matter, deposits and the like are removed.

In step S3005, a cell 50 to be obtained, among cells 50 having been cultured on the placing surface 11, is selected. A cell 50 manifesting a fluorescent protein, a cell 50 manifesting specific structural characteristics or the like is selected as required for specific applications. Once the processing in step S3005 is completed, the operation proceeds to step S3007. In step S3007, the temperature at the support stage 75 is adjusted to an optimal level and the culture vessel 100 is heated to a temperature lower than the temperature at which the entire first gel 14 undergoes denaturation.

In step S3009, the convergence position set near a non-select cell 501 in the first layer 10 is irradiated with the laser light 7. Once the bond between each non-select cell 501 to be detached and the placing surface 11 has become weakened, the operation proceeds to step S3011. In step S3011, the non-select cells 501 are obtained through suction by using a pipette 60. Once the processing in step S3011 is completed, the operation proceeds to step S3013.

In step S3013, a select cell 500 is obtained or cultured. The select cell 500 may be extracted by irradiating the first gel 14 over an area near the select cell 500 with laser light and detaching it with the pipette 60 as in the case of the non-select cells 501, or the select cell 500 may be extracted by pouring a liquid such as PBS, which does not greatly affect the select cell 500, onto the placing surface 11 and picking up the select cell 500 suspended in the liquid. As an alternative, a process for culturing select cells 500 may be started. When select cells 500 are cultured by obtaining non-select cells through the cell acquisition method according to the variation, the state of observation-target select cells 500 alone can be observed in detail over time by adjusting the quantity of cells 50 present on the cell culture substrate 1. Once the select cells 500 are obtained or cultured, the processing ends.

The present invention is not limited to the particulars of the embodiment described above and any other mode conceivable within the scope of the technical teaching of the present invention is also within the scope of the present invention.

Implementation Example

The cell acquisition according to the embodiment was implemented by using HeLa cells as a single-cell model, MDCK cells as a colony-forming cell model and SH-SY5Y cells as a single-cell neuron model.

In addition, two-layer gels with total of the thickness H1 of the first layer 10 and the thickness H2 of the second layer 20 and with the thickness ratio H1/H2 are different to each other were prepared and the success rate in acquisition of cells present in a central area of the culture surface (placing surface 11) of each two-layer gel, among HeLa cells cultured on the two-layer gel, was investigated.

Reagent Preparation

PBS (−)

PBS (−) was prepared by first dissolving NaCl (4.003 g), KCl (0.1003 g), $KH_2PO_4$ (0.1006 g) and $NaH_2PO_4$ (0.575 g) in ion-exchanged water (500 mL) and then sterilizing the mixture in an autoclave.

10× Inorganic Salt Medium $CaCl_2$) anhydride (20.2 mg), $MgCl.6H_2O$ (23.5 mg), KCl (40.4 mg), NaCl (639.7 mg) and $NaH_2PO_4.2H_2O$ (14.1 mg) were added and dissolved in ion-exchanged water (10 mL) and a 10× inorganic salt medium was prepared.

Reconstitution Solution

Reconstitution solution was prepared by adding and dissolving $NaHCO_3$ (219.7 mg) and HEPES (477.12 mg) in NaOH (0.05 M, 10 mL).

Dilute Hydrochloric Acid

Dilute hydrochloric acid (pH=3.0) was prepared by adjusting pH of an HCl aqueous solution (0.05 M) using a pH meter (pH CONDMETER D-54, manufactured by HORIBA Ltd.) to achieve pH=3.0. The 10× inorganic salt medium, the reconstitution solution and the dilute hydrochloric acid (pH=3.0) were each sterilized through a filter (pore diameter 0.20 μm, manufactured by ADVANTEC Ltd.)

Concentrated Gold Nanoparticle (AuNP) Solution 4 mL (2 mL×2) of a Growth solution (see S. Yagi, et al., J Electrochem Soc, 159, H668 (2012)), in which gold nanoparticles had been grown, was placed in a centrifuge tube and was centrifuged for 20 minutes at 25° C. at a rotation rate of 3000 rpm. After the supernatant solution (1.8 mL×2) was removed, ultra-pure water (1.8 mL×2) was added and the solution was centrifuged again under the same conditions. Subsequently, the supernatant solution (1.8 mL×2) was removed and adding ultra-pure water (0.2 mL×2), thereby a concentrated AuNP solution (Au 500 μM) diluting the reducing agent was prepared.

The mean volume diameter of the gold nanoparticles was measured by capturing an image of the gold nanoparticles having been prepared on a transmission electron microscope (JEM—2000F with an acceleration voltage of 200 kV, manufactured by JEOL Ltd.) and executing calculation with an analysis software program (Photomeasure (registered trademark), Kenis Ltd.).

Two-Layer Gel Production

A collagen gel solution (2.1 mL) was prepared by adding the dilute hydrochloric acid (0.42 mL), ultra-pure water (0.7 mL), the 10× inorganic salt medium (0.2 mL) and the reconstitution solution (0.20 mL) in this order into a cell culture substrate (Cellmatrix (registered trademark) 1-A, collagen concentration 0.3 wt. %, pH=3.0, 0.56 mL, manufactured by Nitta Gelatin Co. Limited) while sustaining a cool condition with ice in a clean bench (S-1001 PRV, manufactured by Showa Science Co. Limited). The collagen gel solution, kept cool with ice, was poured into a 96-well plate (manufactured by Nalge Nunc International) and was then incubated for 30 minutes at 37° C. inside a direct heat $CO_2$ incubator. A collagen gel with embedded gold nanoparticles was formed through a similar procedure over the incubated collagen gel by replacing the ultra-pure water (0.70 mL) with the concentrated gold nanoparticle (AuNP) solution (0.70 mL). Subsequently, with the temperature sustained at 37° C., PBS (−) was added at 100 μL/well onto the gel and was incubated for six hours so as to wash the gel.

Cell Seeding and Detachment

HeLa cells (6000 cells/well) dispersed in a DMEM were seeded on the gel prepared as described above and were cultured for 24 hours. The medium was then washed three times with PBS(−). Next, 10 μL of PBS(−) is added on the medium and was incubated under a microscope for three minutes on a 37° C. thermo-plate with an aluminum sheet placed thereupon and then irradiated with light by selecting the smallest setting for the spot diameter. After the irradiation, a manipulator with a bore diameter of 30 μm assembled by combining a three-axis joystick manual micro manipulator (NT-88-V3 MSH, manufactured by Narishige) and a pneumatic micro injector (IM-11-2, manufactured by Narishige) so as to detach cells through suction.

For purposes of light irradiation, a mirror unit (TRITC, manufactured by Nikon) having light-transmitting characteristics for light at 532 nm was installed, through which light at a wavelength of 532 nm was transmitted, was installed with a laser light source (wavelength 532 nm, output 50 mW, manufactured by Sigma Koki) fitted in via a PA (photo activation) epifluorescence illuminator unit (TI-PAU, manufactured by Nikon), whereas cells were observed through fluorescence/phase difference observation and images thereof were captured in conjunction with an inverted fluorescence microscope (ECLIPSE Ti-U, manufactured by Nikon) and an imaging sensor control software program (WraySpect, manufactured by WRAYMER). The cells were observed by using objective lenses (Plan-Fluor, manufactured by Nikon) with magnification factors of 4 and 10.

Similar procedures were carried out for SH-SY5Y cells (6000 cells/well) dispersed in DMEM and MDCK cells (2000 cells/well) dispersed in MEM as well. The MDCK cells were first fluorescent-stained by using Cell Tracker Green CMFDA (10 μM, 10 μL) before they were detached and recovered. Irradiation with laser light was performed a plurality of times from the side where the gel that had not undergone a gold nanoparticle embedding operation was located in correspondence to the colony size so that the irradiation with light would ensure on all the cells forming the colony by keeping the lens in a defocused state. The cell observation was conducted by using a lens with a magnification factor of 4.

Results

Select cells could be obtained in conjunction with the two-layer gels in the implementation example invariably from the HeLa cells, the MDCK cells and the SH-SY5Y cells.

Table 1 presents the results indicating the relationship between the thickness ratio H1/H2 at each two-layer gel and the success rate with which select cells among the HeLa cells were obtained. Provided that the total amount of gel remained constant, a higher success rate was achieved for select cell acquisition in case the thickness ratio H1/H2 was greater, i.e., in case the thickness of the collagen gel having the gold nanoparticles embedded therein was greater by a higher degree than the thickness of the collagen gel which had not undergone a gold nanoparticle embedding operation.

Table 1

Relationship of select cell acquisition success rate to the thickness ratio H1/H2 at gel constituted of collagen gel (AuCol) having gold nanoparticles embedded therein and/or collagen gel (Col) that did not undergo gold nanoparticle embedding operation (N=10 at each cell.

| AuCol (μL) | Col (μL) | thickness of second gel (Col) | thickness ratio H1/H2 | total gel amount (μL) | success rate (%) |
|---|---|---|---|---|---|
| 26 | 52 | 1.7 | 0.5 | 78 | 60 |
| 39 | 39 | 1.2 | 1.0 | 78 | 70 |
| 46.8 | 31.2 | 1.0 | 1.5 | 78 | 70 |
| 49.6 | 28.4 | 0.9 | 1.7 | 78 | 80 |
| 52 | 26 | 0.8 | 2.0 | 78 | 90 |
| 78 | 0 | 0 | (single-layer gel: comparison example) | 78 | 30 |

REFERENCE SIGNS LIST

1 ... cell culture substrate, 7 ... laser light, 10 ... first layer, 11 ... placing surface, 13 ... gold nanoparticle, 14 ... first gel, 20 ... second layer, 24 ... second gel, 70 ... microscope, 100 ... culture vessel, 500 ... select cell, 1000 ... cell acquisition system, H1 ... thickness of first layer, H2 ... thickness of second layer, D ... inner diameter of culture vessel

The invention claimed is:

1. A method for obtaining a cell, placed on a cell culture substrate which is stored in a culture vessel, comprising:

selecting the cell to be obtained among a plurality of cells;

culturing the plurality of cells on a cell placing surface of a first layer of the cell culture substrate that comprises the first layer that includes a first gel in which gold nanoparticles are dispersed, and a second layer that includes a second gel in which the gold nanoparticles are not present or are present in a lower concentration in comparison with the first layer;

weakening a bond between the selected cell cultured on the first layer and the cell placing surface by irradiating with light forward from a side where the second layer is located, a convergence position in the first layer in an area around the selected cell cultured on the cell placing surface of the first layer to induce localized denaturation in the first gel without cell damage; and obtaining the selected cell from the convergence position in the first layer following the irradiation.

2. The method for obtaining the cell according to claim 1, wherein the convergence position in the first layer is within a depth range of less than 100 μm below the selected cell, or within a radius of less than 100 μm from a cell body of the selected cell.

3. The method for obtaining the cell according to claim 1, wherein a thickness ratio of a thickness of the first layer and a thickness of the second layer is greater than 1.5.

* * * * *